US008735641B2

(12) United States Patent
Baeck et al.

(10) Patent No.: US 8,735,641 B2
(45) Date of Patent: May 27, 2014

(54) METHOD FOR SELECTIVE DEALKYLATION OF ALKYL-SUBSTITUTED C9+ AROMATIC COMPOUNDS USING BIMODAL POROUS DEALKYLATION CATALYST AT LOW TEMPERATURE

(75) Inventors: Sung Hyeon Baeck, Seoul (KR); Geon Joong Kim, Seoul (KR); Dong-Kyun Noh, Gyeonggi-do (KR); Tae Young Jang, Jeollabuk-do (KR); Tae-Yun Kim, Incheon (KR); Young Soo Ahn, Ulsan (KR); Chan-ju Song, Ulsan (KR); Sang-Cheol Paik, Ulsan (KR)

(73) Assignees: S-Oil Corporation, Seoul (KR); Inha-Industry Partnership Institute, Incheon (KR)

( * ) Notice: Subject to any disclaimer, the term of this patent is extended or adjusted under 35 U.S.C. 154(b) by 148 days.

(21) Appl. No.: 13/530,414

(22) Filed: Jun. 22, 2012

(65) Prior Publication Data

US 2013/0165727 A1 Jun. 27, 2013

(30) Foreign Application Priority Data

Dec. 22, 2011 (KR) ........................ 10-2011-0140067

(51) Int. Cl.
C07C 4/18 (2006.01)

(52) U.S. Cl.
USPC ....................................... 585/489

(58) Field of Classification Search
USPC ................................. 585/488, 489
See application file for complete search history.

(56) References Cited

U.S. PATENT DOCUMENTS

| | | |
|---|---|---|
| 2,589,621 A | 3/1952 | Lien et al. |
| 2,917,561 A | 12/1959 | Eby |
| 3,201,485 A | 8/1965 | Kovach |
| 3,253,049 A | 5/1966 | Allen et al. |
| 3,267,165 A | 8/1966 | Kimble et al. |
| 3,301,912 A | 1/1967 | Hwang et al. |
| 3,637,880 A | 1/1972 | Burress |
| 3,702,886 A | 11/1972 | Argauer et al. |
| 3,709,979 A | 1/1973 | Chu |
| 3,832,449 A | 8/1974 | Rosinski et al. |
| 3,946,079 A | 3/1976 | Mizutani et al. |
| 4,016,245 A | 4/1977 | Plank et al. |
| 4,046,859 A | 9/1977 | Plank et al. |
| 4,105,541 A | 8/1978 | Plank et al. |
| 4,320,242 A | 3/1982 | Onodera et al. |
| 5,004,854 A | 4/1991 | Yan |
| 5,087,781 A | 2/1992 | Schutz et al. |
| 7,157,397 B2 | 1/2007 | Dalloro et al. |

FOREIGN PATENT DOCUMENTS

| | | |
|---|---|---|
| DE | 25 48 695 A1 | 5/1976 |
| DE | 25 48 697 A1 | 5/1976 |

OTHER PUBLICATIONS

Akhtar, M. N. et al., *Transalkylation of Ethyl Benzene With Triethylbenzene Over ZSM-5 Zerolite Catalyst*, Chemical Engineering Journal, vol. 163, Issues 1-2, Sep. 15, 2010, pp. 98-107.
Chen, X. et al., *Transalkylation of Benzene with 1,2,4-Trimethylbenzene Over Nanosized ZSM-5*, Microporous and Mesoporous Materials, vol. 119, Issue 1-3, Mar. 1, 2009, pp. 171-175.
Li, Y. et al., *Promoted Metal Utilization Capacity of Alkali-Treated Zeolite: Preparation of Zn/ZSM-5 and Its Application in L-Hexene Aromatization*, Applied Catalysis A: General, vol. 360, Issue 1, May 31, 2009, pp. 8-16.
Ogura, M. et al., *Alkali-Treatment Technique—New Method for Modification of Structural and Acid-Catalytic Properties of ZSM-5 Zeolites*, Applied Catalysis A: General, vol. 219, Issues 1-2, Oct. 5, 2001, pp. 33-43.
Song, Y. et al., *Effect of Variations in Pore Structure and Acidity of Alkali Treated ZSM-5 on the Isomerization Performance*; Journal of Molecular Catalysis A: Chemical, vol. 310, Issues 1-2, Sep. 1, 2009, pp. 130-137.
Zhao, L. et al., *Alkali-Treatment of ZSM-5 Zeolites With Different $SiO_2/Al_2O_3$ Ratios and Light Olefin Production by Heavy Oil Cracking*, Fuel Processing Technology: vol. 92, Issue 3, Mar. 2011, pp. 414-420.

Primary Examiner — Thuan D Dang
(74) Attorney, Agent, or Firm — Alston & Bird LLP

(57) ABSTRACT

Disclosed is a method for selective dealkylation of alkyl-substituted $C_9$+ aromatic compounds using a bimodal porous dealkylation catalyst at a low temperature. The catalyst has a bimodal porous structure including both mesopores and micropores. The catalyst includes a crystalline aluminosilicate and a metal. The catalyst is highly active at a low temperature. According to the method, $C_9$+ aromatic compounds substituted with at least one $C_2$+ alkyl group as by-products formed by xylene production can be selectively dealkylated and converted to BTX, etc. on a large scale within a short time. In addition, the method is an environmentally friendly process entailing reduced waste treatment cost when compared to conventional mesitylene production methods. Therefore, high value-added mesitylene can be separated from low value-added $C_9$+ aromatic compounds at lower cost compared to conventional methods. Furthermore, the supported metal catalyst is easy to recover after dealkylation and is recyclable, thereby contributing to reduced cost.

16 Claims, 1 Drawing Sheet

US 8,735,641 B2

METHOD FOR SELECTIVE DEALKYLATION OF ALKYL-SUBSTITUTED C9+ AROMATIC COMPOUNDS USING BIMODAL POROUS DEALKYLATION CATALYST AT LOW TEMPERATURE

CROSS-REFERENCE TO RELATED APPLICATION

This application claims priority to and the benefit of Korean Patent Application No. 10-2011-0140067 filed in the Korean Intellectual Property Office on Dec. 22, 2011, the entire contents of which are incorporated herein by reference.

BACKGROUND OF THE INVENTION

1. Field of the Invention

The present invention relates to a method for selective dealkylation of alkyl-substituted $C_9$+ aromatic compounds using a bimodal porous dealkylation catalyst at a low temperature, and more specifically to a method for selectively dealkylating alkyl-substituted $C_9$+ aromatic compounds at a low temperature by the use of a dealkylation catalyst that has a bimodal porous structure including both mesopores and micropores and includes a crystalline aluminosilicate and a metal.

2. Description of the Related Art $C_9$+ aromatic compounds are produced as by-products of petrochemical processing. Specifically, such $C_9$+ aromatic compounds are produced in the entire petrochemical processes, including naphtha reforming processes, benzene, toluene and xylene (hereinafter referred to simply as 'BTX') production processes and para-xylene production processes, which use crude oil as a starting material.

Particularly, para-xylene is produced via isomerization of $C_8$ aromatics. In this process, disproportionation and transalkylation of xylenes and ethylbenzene occur as side reactions. These side reactions produce 'alkyl-substituted $C_9$+ aromatic compounds,' such as ethyltoluenes, trimethylbenzenes, ethylxylenes and diethylbenzenes. Since most of the by-products are of little practical value, they are used as fuels without further processing or are used, together with toluene, as raw materials in conversion processes to BTX, such as Tatoray$^{SM}$, TransPlus$^{SM}$ and TAC-9, using mordenite-based catalysts.

There is a strong need to recover trimethylbenzenes as $C_9$+ aromatic compounds that are widely used in various industrial fields. Specifically, 1,3,5-trimethylbenzene (mesitylene) and 1,2,4-trimethylbenzene (pseudocumene) are used as solvents of resins, gums, nitrocelluloses, etc., raw materials for lacquers, paints and varnishes, and components of chemical products including antioxidants. In the electronics industry, mesitylene has also been used as a developer for photopatternable silicones due to its solvent properties.

Many mesitylene production methods are known and include, for example, bringing acetone in the liquid phase into contact with sulfuric acid and a catalyst (see U.S. Pat. No. 3,267,165) and bringing acetone in the vapor phase into contact with a catalyst (see U.S. Pat. No. 5,087,781). However, these methods have disadvantages of low conversion of acetone, low mesitylene selectivity, waste water production and complicated processes.

Many methods for producing mesitylene from $C_9$+ aromatic compounds are also known in which ethyltoluenes having a boiling point similar to that of mesitylene are first converted to BTX using a catalyst, followed by extraction in a distillation column. Examples of such methods include a process for the production of mesitylene through isomerization of pseudocumene using ZSM-5, a zeolite catalyst (see U.S. Pat. No. 7,157,397) and a production process in which $C_9$+ aromatic compounds produced during petrochemical processing are further treated with a metal-supported ZSM-6 catalyst, which is a kind of zeolite catalyst, followed by separation into mesitylene and pseudocumene in a distillation column (see U.S. Pat. Nos. 5,004,854 and 4,320,242). However, such methods have disadvantages in that the conversions are low due to the shape selectivity of the catalysts for the reactants and the high reaction temperatures lead to low recovery yields of mesitylene.

PRIOR ART DOCUMENTS

Patent Documents (Patent Documents 1) Conventional mesitylene production methods are classified into a first method for producing mesitylene from acetone and a second method for producing mesitylene using $C_9$+ aromatic streams.

(Patent Documents 2) Specifically, prior art documents based on the first method include U.S. Pat. No. 3,267,165 entitled "Preparation of mesitylene by dehydro-condensation of acetone," U.S. Pat. No. 2,917,561 entitled "Production of mesitylene," U.S. Pat. No. 3,946,079 entitled "Method of condensing ketones," U.S. Pat. No. 3,201,485 entitled "Process for preparing polyalkylated benzenes from alkyl ketones," and U.S. Pat. No. 3,301,912 entitled "Polyalkylated benzenes from ketones."

(Patent Documents 3) Prior art documents based on the second method include U.S. Pat. No. 2,589,621 entitled "Mesitylene manufacture, U.S. Pat. No. 3,253,049 entitled "Production of mesitylene," U.S. Pat. No. 3,637,880 entitled "Isomerization of psuedocumene," U.S. Pat. No. 4,320,242 entitled "Process for selective dealkylation of alkyl-substituted aromatic hydrocarbons," U.S. Pat. No. 5,004,854 entitled "Pseudocumene and mesitylene production and coproduction thereof with xylene," and U.S. Pat. No. 7,157,397 entitled "Process for the production of mesitylene." Particularly, U.S. Pat. No. 4,320,242 discloses a process for selective dealkylation of alkyl-substituted aromatic hydrocarbons in the presence of hydrogen using a dealkylation catalyst, and U.S. Pat. No. 5,004,854 entitled "Pseudocumene and mesitylene production and coproduction thereof with xylene" discloses a process for the production of mesitylene using a catalyst including a crystalline zeolite having a predetermined silica-to-alumina ratio.

Non-Patent Documents (Non-Patent Documents 1) Studies have focused on methods for producing mesitylene from $C_9$+ aromatic compounds. However, these studies are generally based on the use of mordenite or zeolite Y having large-sized pores or the use of alkali-treated ZSM-5 in order to efficiently produce xylene via transalkylation or disproportionation of methyl groups of aromatic compounds.

(Non-Patent Documents 2) Specifically, such studies include: Journal of Molecular Catalysis A: Chemical, Volume 310, Issues 1-2, 1 Sep. 2009, Pages 130-137 "Effect of variations in pore structure and acidity of alkali treated ZSM-5 on the isomerization performance"; Fuel Processing Technology: Volume 92, Issue 3, March 2011, Pages 414-420 "Alkali-treatment of ZSM-5 zeolites with different $SiO_2/Al_2O_3$ ratios and light olefin production by heavy oil cracking"; Applied Catalysis A: General, Volume 219, Issues 1-2, 5 Oct. 2001, Pages 33-43 "Alkali-treatment technique—new method for modification of structural and acid-catalytic properties of ZSM-5 zeolites"; Applied Catalysis A: General, Volume 360, Issue 1, 31 May 2009, Pages 8-16 "Promoted metal utilization capacity of alkali-treated zeolite: Preparation of Zn/ZSM-5 and its application in 1-hexene aromatization"; Microporous and Mesoporous Materials, Volume 119, Issues 1-3, 1 Mar. 2009, Pages 171-175 "Transalkylation of benzene with 1,2, 4-trimethylbenzene over nanosized ZSM-5"; Microporous and Mesoporous Materials, Volume 119, Issues 1-3, 1 Mar. 2009, Pages 171-175 "Transalkylation of benzene with 1,2, 4-trimethylbenzene over nanosized ZSM-5"; and Chemical Engineering Journal, Volume 163, Issues 1-2, 15 Sep. 2010, Pages 98-107 "Transalkylation of ethyl benzene with triethylbenzene over ZSM-5 zeolite catalyst."

SUMMARY OF THE INVENTION

It is an object of the present invention to provide a method for selective dealkylation of $C_9+$ aromatic compounds substituted with at least one alkyl group having two or more carbon atoms at a low temperature by the use of a dealkylation catalyst that has a bimodal porous structure including both mesopores and micropores in a crystalline aluminosilicate catalyst.

In order to accomplish the above object of the present invention, there is provided a method for selective dealkylation of aromatic compounds having at least nine carbon atoms ($C_9+$) substituted with at least one alkyl group having at least two carbon atoms ($C_2+$) at a low temperature, the method including bringing a feed stream including the alkyl-substituted $C_9+$ aromatic compounds into contact with a dealkylation catalyst in the gas phase in the presence of hydrogen wherein the dealkylation catalyst includes a crystalline aluminosilicate and a metal supported on the crystalline aluminosilicate, and wherein the crystalline aluminosilicate has a bimodal porous structure including both mesopores with a diameter of 20 to 100 Å and micropores with a diameter of 4 to 20 Å.

In an embodiment of the present invention, the crystalline aluminosilicate may have a silica/alumina molar ratio of 5 to 100.

In another embodiment of the present invention, the crystalline aluminosilicate having a bimodal porous structure may be prepared by treating a microporous crystalline aluminosilicate with an alkali.

In another embodiment of the present invention, the crystalline aluminosilicate having micropores may be a pentasil zeolite represented by $M_nAl_nSi_{96-n}O_{192}\cdot 16H_2O$ (wherein M is Na or H, and $0<n<27$).

In another embodiment of the present invention, M in $M_nAl_nSi_{96-n}O_{192}\cdot 16H_2O$ may be H.

In an alternative embodiment of the present invention, the crystalline aluminosilicate having a bimodal porous structure may be prepared by introducing micropores into a mesoporous crystalline aluminosilicate during synthesis of the mesoporous crystalline aluminosilicate.

In an alternative embodiment of the present invention, the crystalline aluminosilicate having a bimodal porous structure may be prepared by physically mixing a microporous crystalline aluminosilicate and a mesoporous crystalline aluminosilicate.

In another embodiment of the present invention, the metal may be selected from the group consisting of platinum, palladium, silver, iridium, copper, rhodium, nickel, ruthenium, cobalt, gold, molybdenum, alloys thereof, and mixtures thereof.

In another embodiment of the present invention, the metal may be platinum and the platinum content may be from 0.1 to 1% by weight with respect to the total weight of the dealkylation catalyst.

In another embodiment of the present invention, the volume ratio of the mesopores to the micropores may be from 1:99 to 99:1.

In another embodiment of the present invention, the $C_9+$ aromatic compounds substituted with at least one $C_2+$ alkyl group may include one or more compounds selected from the group consisting of ethylbenzene, ethyltoluenes, trimethylbenzenes, tetramethylbenzenes, diethylbenzenes, ethylxylenes, n-propylbenzene, cumene, and cymenes.

In another embodiment of the present invention, the feed stream may further include xylenes.

In another embodiment of the present invention, the contacting may be performed at a temperature of 250 to 500° C.

In another embodiment of the present invention, the contacting may be performed at a pressure of 0 barg to 10 barg.

In another embodiment of the present invention, the molar ratio of the hydrogen to the feed stream may be 0.5-8:1.

In another embodiment of the present invention, the feed stream may be supplied at a weight hourly space velocity of 0.5 to 10 $hr^{-1}$.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
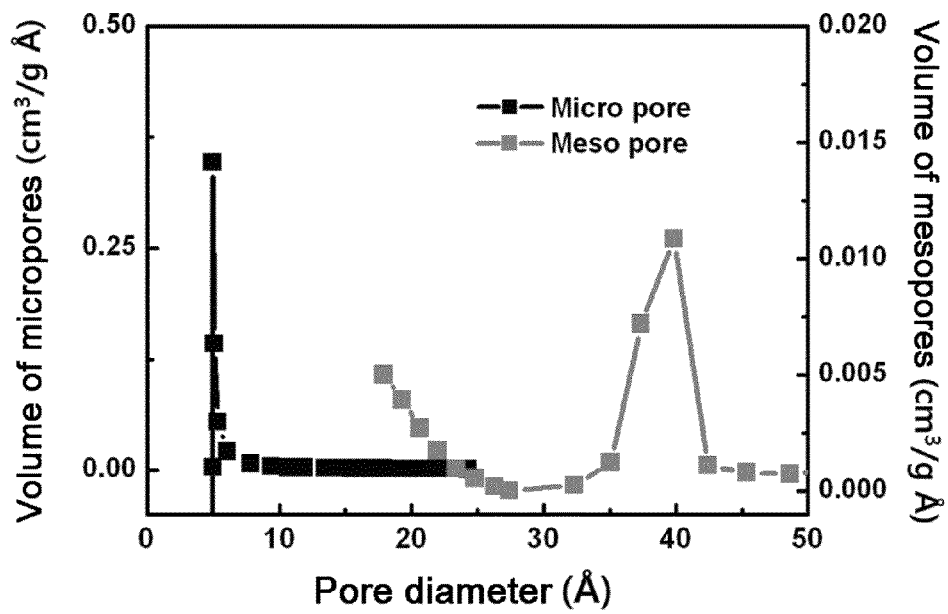
FIG. 1 is a graph showing the distributions of mesopores and micropores in a catalyst of the present invention.
Figure 2:
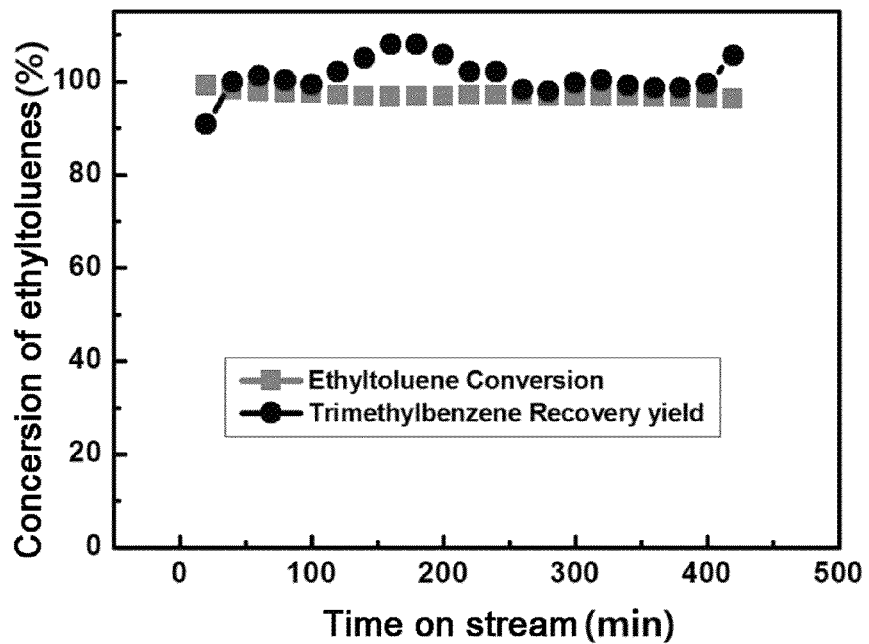
FIG. 2 is a graph showing a variation in the conversion of ethyltoluenes as a function of reaction time in Evaluation Example 4.

The present invention will now be described in more detail with reference to the accompanying drawings.

The present invention provides a method for selective dealkylation of aromatic compounds having at least nine carbon atoms ($C_9+$) substituted with at least one alkyl group having at least two carbon atoms ($C_2+$) at a low temperature, the method including bringing a feed stream including the alkyl-substituted $C_9+$ aromatic compounds into contact with a dealkylation catalyst in the gas phase in the presence of hydrogen wherein the dealkylation catalyst includes a crystalline aluminosilicate and a metal supported on the crystalline aluminosilicate, and wherein the crystalline aluminosilicate has a bimodal porous structure including both mesopores with a diameter of 20 to 100 Å and micropores with a diameter of 4 to 20 Å.

In comparison with conventional catalysts, the dealkylation catalyst of the present invention exhibits markedly improved reaction activity by varying the structure and size of the pores in the catalyst. The coexistence of the mesopores and micropores in the dealkylation catalyst of the present invention results in short diffusion paths of the reactants. In addition, the active sites of the catalyst increase with decreasing silica/alumina ratio, resulting in a considerable increase in the activity of the catalyst. Therefore, the catalyst of the present invention can exert maximal effects at a lower temperature even when used in a smaller amount than conventional catalysts having mesopores or micropores only. Particularly, the catalyst of the present invention selectively dealkylates $C_9+$ aromatic compounds and aromatic hydrocarbons whose alkyl group has two or more carbon atoms in the presence of hydrogen gas. The reaction activity of the catalyst is particularly excellent at low temperatures.

In the dealkylation catalyst of the present invention, the crystalline aluminosilicate preferably has a silica/alumina molar ratio in the range of 5 to 100. Within this range, the density of acid sites in the metal supported on the crystalline aluminosilicate is optimized so that both the recovery yield of trimethylbenzenes and the conversion of ethyltoluenes can be maintained at high levels.

The recovery yield of trimethylbenzenes and the conversion of ethyltoluenes are defined by Equations 1 and 2, respectively:

Recovery yield(mole %)=(The number of moles of trimethylbenzenes recovered)/(The number of moles of trimethylbenzenes supplied)×100  (1)

Conversion(mole %)=(The number of moles of dealkylated ethyltoluenes)/(The number of moles of ethyltoluenes supplied)×100  (2)

In Equation 1, the number of moles of trimethylbenzenes recovered indicates the moles of trimethylbenzenes present in a stream obtained after the feed stream undergoes the contacting step.

The crystalline aluminosilicate having a bimodal porous structure may be prepared i) by treating a microporous crystalline aluminosilicate with an alkali, ii) by introducing micropores into a mesoporous crystalline aluminosilicate during synthesis of the mesoporous crystalline aluminosilicate, or iii) by physically mixing a microporous crystalline aluminosilicate and a mesoporous crystalline aluminosilicate.

Specifically, in the method i), a microporous crystalline aluminosilicate is treated with an alkali, such as an organic or inorganic alkali. This alkali treatment dissociates the silica, leaving mesopores in the microporous crystalline aluminosilicate. The coexistence of micropores and mesopores shortens the diffusion paths of the reactants. In addition, the active sites of the catalyst increase with decreasing silica/alumina ratio, resulting in a considerable increase in the activity of the catalyst. Therefore, the catalyst of the present invention can exert maximal effects at a lower temperature even when used in a smaller amount than conventional catalysts free of mesopores.

The crystalline aluminosilicate having micropores may be a pentasil zeolite represented by $M_nAl_nSi_{96-n}O_{192}.16H_2O$ (wherein M is Na or H, and 0<n<27). The pentasil zeolite represented by $M_nAl_nSi_{96-n}O_{192}.16H_2O$ (wherein M is Na or H, and 0<n<27) may be typified by a ZSM type zeolite developed by Socony-Mobil or a zeta type zeolite developed by Imperial Chemical Industries, Ltd. Examples of such ZSM type zeolites include ZSM-5 (U.S. Pat. No. 3,702,886), ZSM-11 (U.S. Pat. No. 3,709,979), ZSM-12 (U.S. Pat. No. 3,832,449), ZSM-35 (U.S. Pat. No. 4,016,245) and ZSM-38 (U.S. Pat. Nos. 4,046,859 and 4,105,541). Examples of such zeta type zeolites include zeta 1 (German Pat. No. 2,548,697) and zeta 3 (German Pat. No. 2,548,695). It is particularly preferred that M in $M_nAl_nSi_{96-n}O_{192}.16H_2O$ is H. In this case, the pentasil zeolite is represented by $H_nAl_nSi_{96-n}O_{192}.16H_2O$ (0<n<27). A representative example of the pentasil zeolite is HZSM-5 developed by Socony-Mobil.

So long as the catalyst of the present invention has a bimodal porous structure including both mesopores and micropores, the preparation of the catalyst is not limited to the method i) in which a mesoporous structure is introduced by treating a microporous catalyst with an alkali. The catalyst of the present invention may be prepared by the method ii) in which a microporous structure is newly introduced into a mesoporous catalyst. In this case, the catalyst of the present invention may be MCM-36 as a MCM type catalyst. MCM-36 is a porous zeolite composite having a pillared layered structure in which both micropores and mesopores are present. The mesopores are formed between the zeolite structures. MCM-36 is synthesized through swelling and pillaring of MCM-22 as a precursor. Specifically, a surfactant and tetrapropylammonium hydroxide (TPAOH) are first added to the precursor in which structure aligners are filled. The precursor is allowed to swell to increase the interlamellar distances between the structure aligners and polymeric pillars, such as silica and alumina pillars, are then built. Finally, calcination is performed. The catalyst thus obtained has a bimodal porous structure in which 30-35 Å mesopores and 6-9 Å micropores are present together.

Alternatively, the catalyst of the present invention may be produced by the method iii) in which a microporous catalyst is physically mixed with a mesoporous catalyst. In this case, a mesoporous MCM, SBA, TUD or FSM type zeolite may be mixed with the microporous pentasil zeolite. Specifically, MCM-41, SBA-15, TUD-1 or FSM-16 may be used as the mesoporous zeolite. The mixing of a microporous catalyst and a mesoporous catalyst in an optimum volume ratio can simultaneously accomplish characteristics of the two catalysts. Accordingly, the effects of the method iii) are similar to those obtained in the method i) or ii).

As the metal supported on the crystalline aluminosilicate, there may be exemplified at least one metal selected from the group consisting of platinum, palladium, silver, iridium, copper, rhodium, nickel, ruthenium, cobalt, gold, molybdenum and alloys thereof. For example, in the case where a pentasil zeolite represented by $H_nAl_nSi_{96-n}O_{192}.16H_2O$ (0<n<27), for example, HZSM-5, is used as the crystalline aluminosilicate and platinum is used as the supported metal, the catalyst of the present invention may be in the form of Pt/HZSM-5. In this case, the platinum content is preferably in the range of 0.1 to 1% by weight with respect to the total content of the Pt/HZSM-5. Within this content range, the supported metal catalyst becomes highly active and can be produced at low cost.

The volume ratio of the mesopores to the micropores may be from 1:99 to 99:1.

As described above, the method of the present invention includes bringing a feed stream including $C_9+$ aromatic compounds substituted with at least one $C_2+$ alkyl group into contact with the dealkylation catalyst in the gas phase in the presence of hydrogen.

The $C_9+$ aromatic compounds substituted with at least one $C_2+$ alkyl group may include one or more compounds selected from the group consisting of ethylbenzene, ethyltoluenes, trimethylbenzenes, tetramethylbenzenes, diethylbenzenes, ethylxylenes, n-propylbenzene, cumene, and cymenes. Specific examples of such $C_9+$ aromatic compounds include: ethylbenzene; ethyltoluenes, such as p-ethyltoluene, o-ethyltoluene and m-ethyltoluene; trimethylbenzenes, such as 1,2,3-trimethylbenzene, 1,3,5-trimethylbenzene (mesitylene) and 1,2,4-trimethylbenzene (pseudocumene); tetramethylbenzenes, such as 1,2,3,4-tetramethylbenzene, 1,2,3,5-tetramethylbenzene and 1,2,4,5-tetramethylbenzene; diethylbenzenes, such as 1,3-diethylbenzene, 1,4-diethylbenzene and 1,2-diethylbenzene; ethylxylenes, such as 1,2,3-ethylxylene (1-ethyl-2,3-dimethylbenzene), 4,1,2-ethylxylene (4-ethyl-1,2-dimethylbenzene), 2,1,4-ethylxylene (2-ethyl-1,4-dimethylbenzene), 2,1,3-ethylxylene (2-ethyl-1,3-dimethylbenzene), 1,2,4-ethylxylene (1-ethyl-2,4-dimethylbenzene) and 1,3,5-ethylxylene (1-ethyl-3,5-dimethylbenzene); n-propylbenzene; cumene; and cymenes, such as p-cymene, m-cymene and o-cymene. These $C_9+$ aromatic compounds may be used alone or in combination thereof. The feed stream may also further include xylenes.

The feed stream may be brought into contact with the dealkylation catalyst in a fixed bed reactor or a fluidized bed reactor at a temperature of 250° C. to 500° C., for example, a temperature of 330° C. to 410° C. Within this temperature range, energy necessary for the dealkylation reaction is optimally supplied so that side reactions (decyclization or formation of the saturated hydrocarbons) can be suppressed while maintaining the conversion of ethyltoluenes at a high level.

The contacting may be performed at a pressure of 0 barg to 10 barg, for example, 0 psig to 7 psig. Within this pressure range, the reaction rate and the recovery yield of trimethylbenzenes can be maintained at high levels and side reactions can be prevented even when the catalyst is used in a relatively small amount.

The contacting may be performed for 20 minutes to 50 days, for example, 1 hour to 30 days. Within this contact time range, the continuity of the process can be maintained, which is economically advantageous, and the activity of the supported metal catalyst can be maintained at a high level.

The molar ratio of the hydrogen to the feed stream may be from 0.5:1 to 8:1, preferably 1:1 to 3:1, Within this range, side reactions can be prevented while maintaining the activity of the supported metal catalyst at a high level.

The feed stream may be supplied at a weight hourly space velocity (WHSV) of 0.5 to 10 $hr^{-1}$, preferably 3 to 5 $hr^{-1}$. This range provides an optimum contact time between the supported metal catalyst and the feed stream to prevent the occurrence of side reactions while maintaining the conversion of the feed stream (particularly, ethyltoluenes) can be maintained at a high level.

The 'weight hourly space velocity' can be defined by Equation 3:

Weight hourly space velocity of feed stream(WHSV)=
(Weight of feed stream supplied per unit time)/
(Weight of supported metal catalyst)     (3)

In the contacting step, an inert gas, such as nitrogen, may also be further supplied to ensure a smooth supply of the reactants (for example, hydrogen and ethyltoluenes) and the products (for example, trimethylbenzenes).

In the contacting step, the reactants and the products exist in the gas phase and the supported metal catalyst is in the solid phase, which facilitates the recovery of the supported catalyst after dealkylation and enables recycling of the supported catalyst. This can contribute to a reduction in catalyst-related cost.

According to the method of the present invention, the $C_9+$ aromatic compounds substituted with at least one $C_2+$ alkyl group (for example, ethyltoluenes) having boiling points similar to those of trimethylbenzenes (for example, mesitylene) are selectively dealkylated and removed from the feed stream, followed by distillation to separate the trimethylbenzenes from a product stream (i.e. a stream after the contacting step and before the subsequent distillation step) in high purity. Therefore, the $C_9+$ aromatic compounds substituted with at least one $C_2+$ alkyl group, such as ethyltoluenes, can be converted to BTX, etc. by the method of the present invention.

The present invention will be explained in more detail with reference to the following examples. However, these examples are not intended to limit the present invention.

EXAMPLES

Preparative Example 1

Preparation of Bimodal HZSM-5 Having Both Mesopores with Average Diameter of 35-42 Å and Micropores with Average Diameter of 5-6 Å

1 g of sodium hydroxide (NaOH), 0.8 g of sodium aluminate ($NaAlO_2$), 120 ml of distilled water, 6 g of tetrapropylammonium bromide (TPABr) and 25.2 g of silica (KoFran Co., Zeosil-77) were put into a beaker and stirred at room temperature for 30 min. When the mixture became a white opaque sol state, it was transferred to an autoclave reactor (customized) capable of withstanding high temperature and high pressure and heated at 170° C. for 24 hr to obtain Na-ZSM-5 having a silicon/aluminum molar ratio of 43. Then, the Na-ZSM-5 was washed and evaporated using a rotary vacuum evaporator (HS-2001N, Hanshin Science Co.). Subsequently, the moisture-free Na-ZSM-5 was dried at 80° C. for 8 hr. Thereafter, the dried Na-ZSM-5 was heated to 550° C. at a rate of 2° C./min in air and calcined at the same temperature for 5 hr. Thereafter, 10 g of the calcined Na-ZSM-5 was added to 250 ml of a 0.2 M NaOH solution and stirred at 65° C. for 30 min. As a result of the alkali treatment, the Na-ZSM-5 was found to have both mesopores and micropores and have a silicon/aluminum molar ratio of 17. Thereafter, the resulting Na-ZSM-5 was washed and evaporated using a rotary vacuum evaporator (HS-2001N, Hanshin Science Co.). Subsequently, the moisture-free Na-ZSM-5 was dried at 80° C. for 8 hr. Thereafter, the dried Na-ZSM-5 was heated to 550° C. at a rate of 2° C./min in air and calcined at the same temperature for 5 hr. Thereafter, 10 g of the calcined solid was added to an aqueous ammonium chloride solution (i.e. a solution of 4 g of $NH_4Cl$ in 50 mL of distilled water) and heated at 80° C. for 12 hr. Subsequently, the resulting material was washed with distilled water, evaporated, and dried at 80° C. for 24 hr. Thereafter, the dried material was heated to 550° C. at a rate of 2° C./min and calcined at the same temperature for 3 hr, yielding bimodal HZSM-5 having both mesopores with an average diameter of 35-42 Å and micropores with an average diameter of 5-6 Å. The dried material was analyzed by an X-ray diffractometer (DMAX-2500, Rigaku), a scanning electron microscope (S-4300SE, Hitachi) and an inductively coupled plasma spectrometer (Optima 7300DV, PerkinElmer Inc.). The X-ray diffractometer was used to confirm whether or not HZSM-5 was synthesized, the scanning electron microscope was used to determine the average particle size of the HZSM-5, and the inductively coupled plasma spectrometer was used to determine the molar silica/alumina ratio of HZSM-5.

Comparative Preparative Example 1

Preparation of HZSM-5 Having Micropores with Average Diameter of 5-6 Å

HZSM-5 was prepared in the same manner as in Preparative Example 1, except that 1 g of sodium hydroxide (NaOH), 0.8 g of sodium aluminate ($NaAlO_2$), 120 ml of distilled water, 6 g of tetrapropylammonium bromide (TPABr) and 25.2 g of silica (KoFran Co., Zeosil-77) were put into a beaker and stirred at room temperature for 24 hr, and no alkali treatment was conducted. The HZSM-5 was found to have micropores with an average diameter of 5-6 Å and have a silica/alumina molar ratio of 56.

Preparative Example 2

Preparation of Bimodal Pt/HZSM-5 Having Both Mesopores with Average Diameter of 35-42 Å and Micropores with Average Diameter of 5-6 Å

10 g of HZSM-5 prepared in Preparative Example 1 and 0.052 g of $Pt(NH_3)Cl_2$ were added to 30 mL of distilled water and stirred at 50° C. for 8 hr. The resulting mixture was washed with distilled water, evaporated, dried at 100° C. for 8 hr, and calcined at 200° C. for 16 hr. Then, the calcined material was heated to 400° C. at a rate of 2° C./min under a hydrogen atmosphere and maintained at the same temperature for 2 hr, yielding a bimodal Pt/HZSM-5 catalyst having a Pt content of 0.3 wt %. The catalyst was found to have both mesopores with an average diameter of 35-42 Å and micropores with an average diameter of 5-6 Å.

Comparative Preparative Example 2

Preparation of Pt/HZSM-5 Having Micropores with Average Diameter of 5-6 Å

A Pt/HZSM-5 catalyst was prepared in the same manner as in Preparative Example 2, except that the HZSM-5 prepared in Comparative Preparative Example 1 was used instead of the HZSM-5 prepared in Preparative Example 1. The Pt/HZSM-5 catalyst was found to have micropores with an average diameter of 5-6 Å and a Pt content of 0.3 wt %.

Evaluation Example 1

Hydrodealkylation Using Bimodal Pt/HZSM-5 Catalyst Having Both Mesopores with Average Diameter of 35-42 Å and Micropores with Average Diameter of 5-6 Å: Influence of Reaction Temperature Ethyltoluenes included in a feed stream having the composition shown in Table 1 were hydrodealkylated using the Pt/HZSM-5 catalyst prepared in Preparative Example 2 in accordance with the following procedure. First, the Pt/HZSM-5 catalyst was thermally treated at 400° C. under a hydrogen atmosphere for 1.5 hr to reduce platinum oxides present in the catalyst. Thereafter, 0.17 g of the Pt/HZSM-5 catalyst was filled on quartz wool closing one side of a cylindrical stainless steel reactor (inner diameter=0.36 cm, length=0.67 cm), and another quartz wool was placed thereon to fix the catalyst. An inlet line and an outlet line were connected to both ends of the reactor. Thereafter, the temperatures of the inlet and outlet lines were maintained at 220° C. The temperature of the reactor (i.e. reaction temperature) was changed as shown in Table 2 and the pressure of the reactor was maintained at atmospheric pressure. Thereafter, the feed stream was fed into the reactor using a syringe pump (781100, KDScientific) while continuously introducing hydrogen gas (purity=99.999 mole %) at a constant rate of 4 mm/min into the reactor. The feed stream was fed at a fixed weight hourly space velocity (WHSV) of 3 $hr^{-1}$. The feed stream/hydrogen gas molar ratio was set to 0.5. The reaction was continued for 3 hr. A product stream discharged from the reactor was cooled using a cold trap to obtain a solid product. After the solid product was dissolved in tetrahydrofuran, element analysis was conducted using a gas chromatograph (6890A, Agilent). From the element analysis results, the conversion of ethyltoluenes and the recovery yield of trimethylbenzenes were calculated by Equations 2 and 3, respectively. The results are shown in Table 2.

TABLE 1

| | | Ethyltoluenes | | Trimethylbenzenes | | | Tetramethylbenzenes | | |
| | | | | | | 1,2,3- | 1,2,4,5- | 1,2,3,5- | 1,2,3,4- |
| | Xylenes | p-Ethyltoluene | o-Ethyltoluene | Mesitylene | Psuedocumene | Trimethyl-benzene | Tetramethyl-benzene | Tetramethyl-benzene | Tetramethyl-benzene |
| Composition (mole %) | 3.50 | 7.48 | 0.93 | 18.68 | 53.01 | 7.27 | 3.38 | 4.52 | 1.23 |

TABLE 2

| Reaction temp. (° C.) | Conversion of ethyltoluenes (mole %) | Recovery yield of trimethylbenzenes (mole %) |
| --- | --- | --- |
| 330 | 98.4 | 90.1 |
| 370 | 99.0 | 86.8 |
| 410 | 99.4 | 80.0 |
| 450 | 99.5 | 53.5 |

Referring to the results in Table, 2, most of the ethyltoluenes were converted at all temperatures of the reactor and the recovery yield of the trimethylbenzenes was increased with decreasing temperature.

Evaluation Example 2

Hydrodealkylation Using Bimodal Pt/HZSM-5 Catalyst Having Both Mesopores with Average Diameter of 35-42 Å and Micropores with Average Diameter of 5-6 Å: Influence of Reaction Pressure Hydrodealkylation was carried out in the same manner as in Evaluation Example 1, except that the temperature of the reactor was fixed to 410° C. and the pressure of the reactor was changed as shown in Table 2 using a backpressure regulator installed in the outlet line. According to the same procedure as described in Evaluation Example 1, solid products were obtained and analyzed, and the conversions of ethyltoluenes and the recovery yields of trimethylbenzenes were calculated. The results are shown in Table 3.

TABLE 3

| Reaction pressure (barg) | Conversion of ethyltoluenes (mole %) | Recovery yield of trimethylbenzenes (mole %) |
| --- | --- | --- |
| 0 | 99.4 | 80.0 |
| 3 | 98.7 | 66.6 |

TABLE 3-continued

| Reaction pressure (barg) | Conversion of ethyltoluenes (mole %) | Recovery yield of trimethylbenzenes (mole %) |
|---|---|---|
| 6 | 99.6 | 64.1 |
| 9 | 99.6 | 62.7 |

Referring to the results in Table, 3, most of the ethyltoluenes were converted at all pressures of the reactor and the recovery yield of the trimethylbenzenes was increased with decreasing pressure.

Evaluation Example 3

Hydrodealkylation Using Bimodal Pt/HZSM-5 Catalyst Having Both Mesopores with Average Diameter of 35-42 Å and Micropores with Average Diameter of 5-6 Å: Influence of Weight Hourly Space Velocity of Feed Stream Hydrodealkylation was carried out in the same manner as in Evaluation Example 1, except that the Pt/HZSM-5 catalyst prepared in Preparative Example 2 was filled in the amounts as shown in Table 4 to control the weight hourly space velocity of the feed stream and the temperature of the reactor was fixed to 410° C. According to the same procedure as described in Evaluation Example 1, solid products were obtained and analyzed, and the conversions of ethyltoluenes and the recovery yields of trimethylbenzenes were calculated. The results are shown in Table 4.

TABLE 4

| WHSV of feed stream (hr$^{-1}$) | Amount of catalyst filled (g) | Conversion of ethyltoluenes (mole %) | Recovery yield of trimethylbenzenes (mole %) |
|---|---|---|---|
| 1 | 0.52 | 99.5 | 78.2 |
| 3 | 0.17 | 99.4 | 80.0 |
| 5 | 0.10 | 96.0 | 90.9 |

Referring to the results in Table 4, the conversion of the ethyltoluenes was increased substantially but the recovery yield of the trimethylbenzenes was decreased with decreasing WHSV of the feed stream.

Evaluation Example 4

Hydrodealkylation Using Bimodal Pt/HZSM-5 Catalyst Having Both Mesopores with Average Diameter of 35-42 Å and Micropores with Average Diameter of 5-6 Å

In Evaluation Example 4 and Comparative Evaluation Example 1, the performance of the catalyst prepared in Preparative Example 2 was compared with that of the catalyst prepared in Comparative Preparative Example 2. Hydrodealkylation was carried out in the same manner as in Evaluation Example 1, except that the pressure of the reactor was changed to 3 barg and 3.5 barg using a backpressure regulator installed in the outlet line, the temperature of the reactor was fixed to 330° C. and the WHSV of the feed stream was fixed to 4 hr$^{-1}$. According to the same procedure as described in Evaluation Example 1, solid products were obtained and analyzed, and the conversions of ethyltoluenes and the recovery yields of trimethylbenzenes were calculated. The results are shown in Table 5.

TABLE 5

| Reaction pressure (barg) | Conversion of ethyltoluenes (mole %) | Recovery yields of trimethylbenzenes (mole %) |
|---|---|---|
| 3 | 96.6 | 99.8 |
| 3.5 | 98.3 | 94.9 |

As can be seen from the results in Table 5, the application of an appropriate pressure in a relatively small amount of the catalyst and at a relatively low temperature led to high conversions of the ethyltoluenes and high recovery yields of the trimethylbenzenes. In addition, the conversion of the ethyltoluenes was increased but the recovery yield of the trimethylbenzenes was decreased with increasing reaction pressure.

Comparative Evaluation Example 1

Hydrodealkylation Using Pt/HZSM-5 Catalyst Having Micropores with Average Diameter of 5-6 Å

Hydrodealkylation was carried out in the same manner as in Evaluation Example 4, except that the Pt/HZSM-5 catalyst prepared in Comparative Preparative Example 2 was used. According to the same procedure as described in Evaluation Example 1, solid products were obtained and analyzed, and the conversions of ethyltoluenes and the recovery yields of trimethylbenzenes were calculated. The results are shown in Table 6.

TABLE 6

| Reaction pressure (barg) | Conversion of ethyltoluenes (mole %) | Recovery yields of trimethylbenzenes (mole %) |
|---|---|---|
| 3 | 64.1 | 94.1 |
| 3.5 | 75.8 | 90.7 |

As can be seen from the results in Table 6, the conversion of the ethyltoluenes and the recovery yield of the trimethylbenzenes were lower when the prior art catalyst was used than when the inventive catalyst was used under the same conditions as shown in Table 5. As in Evaluation Example 4, the conversion of the ethyltoluenes was increased but the recovery yield of the trimethylbenzenes was decreased with increasing reaction pressure.

For comparison, Table 7 shows data taken from the conversions of ethyltoluenes and the recovery yields of trimethylbenzenes obtained in Evaluation Example 4 and Comparative Evaluation Example 1.

TABLE 7

|   | Reaction temp. (° C.) | Reaction pressure (barg) | WHSV of feed stream (hr$^{-1}$) | Conversion of ethyltoluenes (mole %) | Recovery yield of trimethylbenzenes (mole %) |
|---|---|---|---|---|---|
| Example 4 | 330 | 3 | 4 | 96.6 | 99.8 |
|   |   | 3.5 |   | 98.3 | 94.9 |

TABLE 7-continued

| | Reaction temp. (° C.) | Reaction pressure (barg) | WHSV of feed stream (hr$^{-1}$) | Conversion of ethyltoluenes (mole %) | Recovery yield of trimethylbenzenes (mole %) |
|---|---|---|---|---|---|
| Comparative Example 1 | | 3 3.5 | | 64.1 75.8 | 94.1 90.7 |

As can be seen from the results in Table 7, the conversions of the ethyltoluenes and the recovery yields of the trimethylbenzenes were above 94% in Evaluation Example 4 using the inventive bimodal porous Pt/HZSM-5 catalyst having both mesopores with an average diameter of 35-42 Å and micropores with an average diameter of 5-6 Å. In contrast, the conversions of the ethyltoluenes and the recovery yields of the trimethylbenzenes obtained using the prior art Pt/HZSM-5 catalyst having micropores with an average diameter of 5-6 Å in Comparative Evaluation Example 1 were lower than those obtained in Evaluation Example 4. Particularly, there was a significant difference in the conversion of ethyltoluenes.

As is apparent from the foregoing, according to the present invention, $C_9+$ aromatic compounds substituted with at least one $C_2+$ alkyl group as by-products formed in the course of xylene production can be selectively dealkylated and converted to BTX, etc. on a large scale within a short time. In addition, the method of the present invention is an environmentally friendly catalytic process entailing greatly reduced waste treatment cost when compared to conventional mesitylene production methods. Therefore, high value-added mesitylene, whose demand is expected to increase in various industrial fields, can be separated from low value-added $C_9+$ aromatic compounds at very low cost by the present invention in comparison with other inventions. Furthermore, the supported metal catalyst is easy to recover after dealkylation and is recyclable. This can contribute to a reduction in catalyst-related cost.

Although preferred embodiments of the present invention have been described with reference to the drawings and examples, the embodiments are provided for illustrative purposes only. Those skilled in the art will appreciate that various modifications and equivalents can be made to these embodiments can be made without departing from the spirit of the invention. Accordingly, the scope of the present invention should be defined by the claims that follow.

What is claimed is:

1. A method for selective dealkylation of aromatic compounds having at least nine carbon atoms ($C_9+$) substituted with at least one alkyl group having at least two carbon atoms ($C_2+$) at a low temperature, the method comprising bringing a feed stream comprising the alkyl-substituted $C_9+$ aromatic compounds into contact with a dealkylation catalyst in the gas phase in the presence of hydrogen wherein the dealkylation catalyst comprises a crystalline aluminosilicate and a metal supported on the crystalline aluminosilicate, and wherein the crystalline aluminosilicate has a bimodal porous structure comprising both mesopores with a diameter of 20 to 100 Å and micropores with a diameter of 4 to 20 Å.

2. The method according to claim 1, wherein the crystalline aluminosilicate has a silica/alumina molar ratio of 5 to 100.

3. The method according to claim 1, wherein the crystalline aluminosilicate having a bimodal porous structure is prepared by treating a microporous crystalline aluminosilicate with an alkali.

4. The method according to claim 3, wherein the crystalline aluminosilicate having micropores is a pentasil zeolite represented by $M_nAl_nSi_{96-n}O_{192}.16H_2O$ (M is Na or H, and 0<n<27).

5. The method according to claim 4, wherein M in $M_nAl_nSi_{96-n}O_{192}.16H_2O$ is H.

6. The method according to claim 1, wherein the crystalline aluminosilicate having a bimodal porous structure is prepared by introducing micropores into a mesoporous crystalline aluminosilicate during synthesis of the mesoporous crystalline aluminosilicate.

7. The method according to claim 1, wherein the crystalline aluminosilicate having a bimodal porous structure is prepared by physically mixing a microporous crystalline aluminosilicate and a mesoporous crystalline aluminosilicate.

8. The method according to claim 1, wherein the metal is selected from the group consisting of platinum, palladium, silver, iridium, copper, rhodium, nickel, ruthenium, cobalt, gold, molybdenum, alloys thereof, and mixtures thereof.

9. The method according to claim 1, wherein the metal is platinum and the platinum content is from 0.1 to 1% by weight with respect to the total weight of the dealkylation catalyst.

10. The method according to claim 1, wherein the volume ratio of the mesopores to the micropores is from 1:99 to 99:1.

11. The method according to claim 1, wherein the $C_9+$ aromatic compounds substituted with at least one $C_2+$ alkyl group comprise one or more compounds selected from the group consisting of ethylbenzene, ethyltoluenes, trimethylbenzenes, tetramethylbenzenes, diethylbenzenes, ethylxylenes, n-propylbenzene, cumene and cymenes.

12. The method according to claim 1, wherein the feed stream further comprises xylenes.

13. The method according to claim 1, wherein the contacting is performed at a temperature of 250 to 500° C.

14. The method according to claim 1, wherein the contacting is performed at a pressure of 0 barg to 10 barg.

15. The method according to claim 1, wherein the molar ratio of the hydrogen to the feed stream is 0.5-8:1.

16. The method according to claim 1, wherein the feed stream is supplied at a weight hourly space velocity of 0.5 to 10 hr$^{-1}$.

* * * * *